United States Patent [19]

Kaufhold et al.

[11] Patent Number: 4,990,682
[45] Date of Patent: Feb. 5, 1991

[54] PROCESS FOR THE PREPARATION OF 5-CHLORO-2-PENTANONE

[75] Inventors: Manfred Kaufhold, Marl; Werner Otte, Dorsten, both of Fed. Rep. of Germany

[73] Assignee: Huels AG, Marl, Fed. Rep. of Germany

[21] Appl. No.: 439,688

[22] Filed: Nov. 21, 1989

[30] Foreign Application Priority Data

Feb. 2, 1989 [DE] Fed. Rep. of Germany ....... 3903029

[51] Int. Cl.$^5$ .............................................. C07C 45/59
[52] U.S. Cl. .................................... 568/386; 549/453; 549/454
[58] Field of Search ............... 568/885, 386, 404, 386; 549/453, 454

[56] References Cited

U.S. PATENT DOCUMENTS 2,782,243 2/1957 Hess et al. ........................... 568/885
4,433,175 2/1984 Kaufhold ........................... 568/885
4,533,648 8/1985 Corrigan et al. .................... 568/885

OTHER PUBLICATIONS

Williamann et al., Helveutia Chem. Akta, vol. 32, p. 2151 (1949).
Ishimaru, Chem. Abst., vol., #17728 (1957).

Primary Examiner—James H. Reamer
Attorney, Agent, or Firm—Oblon, Spivak, McClelland, Maier & Neustadt

[57] ABSTRACT

A process for the preparation of 5-chloro-2-pentanone starting from a ketal of a levulinic ester, followed by hydrogenation, and then reaction with hydrochloric acid. The process involves first purifying the ketal of the levulinic ester by distillation, making the hydrogenation catalysts for the ketal alkaline, and reacting the 3-(2-methyl-1,3-dioxolan-2-yl)propan-1-ol formed in this hydrogenation with hydrochloric acid to obtain 5-chloro-2-pentanone.

6 Claims, No Drawings

PROCESS FOR THE PREPARATION OF 5-CHLORO-2-PENTANONE

BACKGROUND OF THE INVENTION

1. Field of the Invention:

This invention concerns a process for the preparation of 5-chloro-2-pentanone by ketalization of a levulinic acid ester with ethylene glycol to obtain (1) catalytic hydrogenation of (1) to obtain 3-(2-methyl-1, 3-dioxolan-2-yl)propan-1-ol (2), and reaction of this dioxolane derivative with hydrochloric acid acid to obtain 5-chloro-2-pentanone (3).

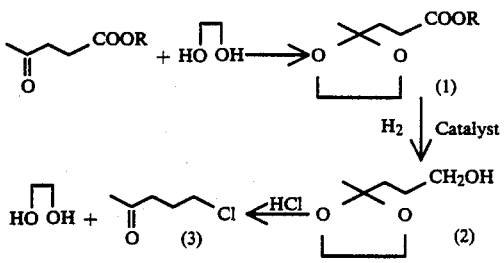

2. Discussion of the Background:

Syntheses of 5-chloro-2-pentanone have long been known from the literature. The most popular method is the reaction of alpha-acetyl-gamma-butyrolactone with hydrogen chloride (Org. Synth. CV4, 1963, 597). A drawback in this procedure is the use of costly alpha-acetyl-gamma-butyrolactone, which is available by ester condensation of gamma-butyrolactone, for example, and ethyl acetate in the presence of equimolar amounts of metallic sodium.

Numerous authors describe the reaction of 4-hydroxy-2-pentanone with hydrogen chloride to obtain (3), for example Ishimaru, Chem. Abstr. 1957, 17728. 5-Hydroxy-2-pentanone is also a costly chemical that makes the process uneconomical.

On the other hand, L. Willimann and H. Schinz, Helvetia Chem. Akta, 32, 1949, 2151, use inexpensive ethyl levulinate (R = $C_2H_5$), ketalize it with ethylene glycol, and reduce (1) with a large excess of metallic sodium and ethanol to obtain (2). The generally high chlorine content of the levulinic ester derived from its preparation does not interfere with this method of hydrogenation of the ketal. A drawback in this procedure is the use of costly metallic sodium that can be handled only with caution, and the disposal of the waste products formed from it.

All known processes for preparing 5-chloro-2-pentanone either start with costly starting materials or use expensive chemicals in large amounts during the synthesis whose disposal involves environmental protection problems. A process by which the ketal of a levulinic ester (1) be hydrogenated catalytically under ordinary conditions to obtain (2) is desirable.

The reaction of (2) with hydrochloric acid to obtain (3) should present no problems, since according to Willimann and Schinz, 5-hydroxy-2 pentanone can be prepared from (2) by reaction with water and a small amount of acid, and its reaction with hydrochloric acid to obtain 5-chloro-2-pentanone (3), as mentioned above, is likewise described in the literature.

The problem, therefore, is to develop a process by which 3-(2-methyl-1,3-dioxolan-2-yl)propan-1-ol (2) can be prepared at low technical cost and without using expensive reagents, from which 5-chloro-2-pentanone is obtained by reaction with hydrochloric acid. 5-Chloro2-pentanone has great economic importance as a pharmaceutical raw material and as the starting material for the production of cyclopropyl methyl ketone.

When the ketal of a levulinic ester (1) is hydrogenated catalytically by the customary methods of ester hydrogenation, for example with a commercial copper chromite catalyst, 1, 4-pentanediol is obtained, i.e., the dioxolane ring is opened by hydrogenolysis. A need continues to exist, therefore, for a new and economical method for preparing 5-chloro-2-pentanone.

SUMMARY OF THE INVENTION

Accordingly, one object of the invention is to provide a process for the economical production of 5-chloro-2-pentanone.

This and other objects which will become apparent from the following specification have been achieved by the present process for the preparation of 5-chloro-2pentanone starting from levulinic ester, which is characterized by:

a) ketalization of levulinic ester $CH_3$—CO—CH 2—$CH_2$—COOR, in which R is $CH_3$, $C_2H_5$, $C_3H_7$, and $C_4H_9$, with ethylene glycol by a known method;

b) purification of the ketal by distillation to a chlorine content $\leq 10$ ppm;

c) hydrogenation of the purified ketal with a conventional hydrogenation catalyst that has previously been treated with an alcoholic alkali metal and/or alkaline earth metal hydroxide solution, to obtain 3(2-methyl-1, 3-dioxolan-2-yl)propan-1-ol, and d) reaction of the 3-(2-methyl-1,3-dioxolan-2-yl) propan-1-ol with hydrochloric acid to obtain 5-chloro-2-pentanone.

DETAILED DESCRIPTION OF THE PREFERRED EMBODIMENTS

The chemical reactions occurring in the process of the present invention are shown below.

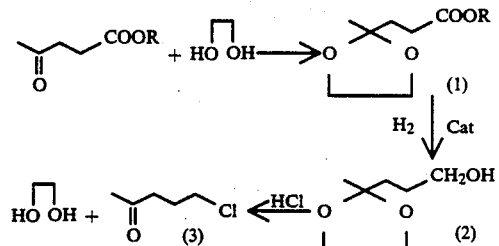

The catalyst used to prepare compound (2) from compound (1) is adjusted to be alkaline. Surprisingly, it has been found that the hydrogenation of compound (1) under otherwise identical conditions proceeds to produce the desired compound (2) if the catalyst is adjusted to be alkaline.

The concentration (normality) of the alcoholic alkali metal and/or alkaline earth metal hydroxide solution is 0.001 to 0.5, preferably about 0.005 to 0.01, and most preferably about 0.05.

Suitable alkali metal and alkaline earth metal hydroxides are LiOH, NaOH, KOH, $Mg(OH)_2$, $Ca(OH)_2$, $Sr(OH)_2$, and $Ba(OH)_2$, with NaOH, KOH, and $Ba(OH)_2$ being particularly preferred.

The treatment of the catalyst with the alcoholic metal hydroxides is generally conducted at room temperature and atmospheric pressure, although other temperatures and pressures both above and below these values may be used. Treatment time ranges from about 0.5–2.0 hrs. Although longer times may be used, longer times are generally unnecessary.

Suitable alcohols are lower alcohols having up to 6 carbon atoms. Methanol and ethanol are preferred.

The starting material (1) is prepared, for example, by the reaction of ethylene glycol with butyl levulinate in the presence of phosphoric acid as a catalyst and cyclohexane as an azeotropic solvent to remove the water. After distillation, the relatively pure ketal of butyl levulinate is obtained with a low chlorine content of $\leq 10$ ppm. This effect is surprising, since the chlorine content of the butyl ester used is always very high, for example 67 ppm, because of its method of preparation. Products with such high chlorine content (> 10 ppm) cannot be hydrogenated with conventional hydrogenation catalysts, since the catalyst quickly loses its activity due to the chlorine content, and corrosion would be expected in high-pressure reactors.

The subsequent hydrogenation is accomplished with conventional hydrogenation catalysts such as copper chromite catalysts (for example, Mallinckrodt E 406, Harshaw 1107, Girdler G 99), which are treated in accordance with the invention and used in conventional amounts.

Analysis of the hydrogenation product by gas chromatography shows a surprisingly high conversion of greater than 99% and selectivity of greater than 95%. The hydrogenation product is isolated by conventional distillation.

5-Chloro-2-pentanone is prepared from (2) in the same way as described in the literature for 5-hydroxy-2-pentanone. Concentrated hydrochloric acid is cooled to about 0° C, and (2) is added slowly at this temperature. The mixture is then distilled, with a 2-phase mixture of 5-chloro-2-pentanone and water forming, until the distillate obtained is singlephased, i.e., only water distills off. The distilled mixture is processed by conventional extraction followed by distillation.

Other features of the invention will become apparent in the course of the following descriptions of exemplary embodiments which are given for illustration of the invention and are not intended to be limiting thereof.

EXAMPLES

Example 1a: Ketalization of Levulinic Ester and Purification by Distillation A glass apparatus is used that consists of a 3-necked flask with stirrer, thermometer, and water separator with reflux condenser.

The starting materials are:
1,054 g (6 moles) butyl levulinate (98.1%, chlorine content 67 ppm)
435 g (7 moles) ethylene glycol
12 g phosphoric acid (85%)
600 g cyclohexane as solvent (codistillate).

The mixture is heated to boiling with stirring. A temperature of 100° C. is reached and the water formed is removed by codistillation. When the temperature rises, for example after about 5.5 hours, 200 g of cyclohexane is replenished through a dropping funnel. After 6.5 hours, 2.5 ml of phosphoric acid (85%) is added, and the water removal is complete after 13.5 hours. After cooling to room temperature, 500 g of 10% sodium hydroxide solution is added to the crude product with stirring, and the phases are then separated:

| Oil phase | 1,652 g |
|---|---|
| aqueous phase | 692 g |

3 g of sodium carbonate is added to the oil phase, and it is distilled through a 0.5 m column packed with Multifill packaging material (Charge: 1,652 g).

| Fraction Number | Temperatures (°C.) Head | Bottoms | Weight (g) | Pressure (hPa) | Reflux Ratio |
|---|---|---|---|---|---|
| 1 | 40–58 | 56–124 | 446 | 300 | 1:1 |
| 2 | 25–101 | 104–162 | 27 | 133 30 | 1:1 |
| 3 | 127–130 | 158–160 | 57 | 30 | 1:1 3:1 |
| 4 | 140–148 | 160 | 12 | 30 | 3:1 |
| 5 | 150–152 | 156–162 | 993 | 30 | 1:1 3:1 |
| Residue | | | 23 | | |
| Cold Trap | | | 80 | | |
| | | | 1,638 | | |

Fraction 1 is cyclohexane and is discarded. Fraction 2 is 99% n-butanol, and Fraction 3 is 93% unreacted butyl levulinate. Fraction 4 is an intermediate fraction with 75% levulinic ester and 22% of the ketal of this ester.

The main fraction (Fraction 5) contains the desired ketal with a purity of 99.6%. Its low chlorine content of 6 ppm makes catalytic hydrogenation possible. The ketal ester yield is calculated to be about 77% based on the charge.

Example 1b: Hyrdogenation of the Purified Ketal 100 ml per hour of the ketal of levulinic ester (1) purified by distillation is hydrogenated in a continuous flow-through hydrogenation reactor with a volume of 400 ml, at a total pressure of 300 hPa at 200° C, on a commercial copper chromite catalyst from the Mallinckrodt Company. The catalyst was treated with 2 liters of 0.05 N alcoholic KOH before the hydrogenation.

Analysis by gas chromatography showed the hydrogenation product had the following compensation:

| Butanol | 44% |
|---|---|
| (2) | 52% |
| (1) | 0.3% |

Distillation provided 3-(2-methyl-1,3-dioxolan-2-yl) propan-1-ol (2) with a boiling point of 127° C. at 30 mbar with 99% purity. The conversion in the hydrogenation was therefore above 99% and the selectivity was above 95%.

Example 1c: Reaction of the Hydrogenated Ketal with Hydrochloric Acid

A glass apparatus is used which consists of a 3-necked flask with stirrer, thermometer, dropping funnel, and distillation apparatus.

The starting materials are:
750 ml conc. hydrochloric acid
292.4 g (2 moles) 3-(2-methyl-1,3-dioxolan-2-yl)-propan-1-ol (2)

The concentrated hydrochloric acid is placed in the flask and cooled to 0° C. (2) is then added slowly over a period of half an hour with stirring, with the temperature being held at 0° C. by strong cooling. The cooling bath is then removed, and the temperature is increased over a period of half an hour until the product distills off. The distillate is first single-phased and then two-phased. When no more second phase is obtained, the distillation is stopped. The phases are then separated, the aqueous phase is extracted with cyclohexane, and the extract and the organic phase are combined and distilled. The boiling point of 5-chloropentanone at 30 hPa is 77° C., yield = 180 g, purity = 98%, i.e., yield based on charge = 73% of the theoretical value.

Example 1d

The apparatus described in Example 1c is used, and the reaction described above is carried out at 0° C. After the cooling bath is removed, 200 g of toluene are added, and the mixture is then heated to boiling under reflux.

After half an hour of boiling, the mixture is cooled, the phases are separated, and the aqueous phase is extracted 3 times with toluene. The toluene phases are combined and distilled. Yield based on charge: 92% of the theoretical.

Example 2b

The method is the same as in Example 1b, but the catalyst is treated with 10 liters of 0.01 N alcoholic KOH solution before the hydrogenation. The result of hydrogenation conforms to that from Example 1b.

Example 3b

The method is the same as in Example 1b, but the catalyst is treated with 40 ml of 0.25 N alcoholic NaOH solution before the hydrogenation. The result of hydrogenation conforms to that from Example 1b.

Example 4b: Comparison

The method is the same as in Example 1b, but the catalyst is treated with 2 liters of 0.05 N alcoholic Ba(OH)$_2$ solution before the hydrogenation. The result of hydrogenation conforms to that from Example 1b.

Example 4: Comparison

The hydrogenation was carried out as in Example 1b, but the catalyst was not made alkaline.

Analysis by gas chromatography showed the hydrogenation product had the following composition (principal components):

| | |
|---|---|
| Butanol | 51% |
| 1,4-Pentanediol | 46% |
| 3-(2-methyl-1,3-dioxolan-2-yl)propan-1-ol | 0.5% |

Obviously, numerous modifications and variations of the present invention are possible in light of the above teachings. It is therefore to be understood that within the scope of the appended claims, the invention may be practiced otherwise than as specifically described herein.

What is claimed is:

1. A process for the preparation of 5-chloro-2-pentanone from levulinic ester, comprising the steps of:
   (a) ketalizing a levulinic ester having the formula $CH_3-CO-CH_2-CH_2-COOR$, in which R is $CH_3$, $C_2H_5$, $C_3H_7$, or $C_4H_9$, with ethylene glycol and removing water with an azeotropic solvent,
   (b) purifying the ketal prepared by distillation to a chlorine content $\leq$ 10 ppm,
   (c) hydrogenating the purified ketal with a hydrogenation catalyst that has been treated with an 0.001-0.5 normal alcoholic alkali metal hydroxide solution, 0.001-0.5 normal alcoholic alkaline earth metal hydroxide solution or mixture thereof, to obtain 3-(2-methyl-1, 3-dioxolan-2-yl) propan-1-ol, and
   (d) reacting the 3-(2-methyl-1, 3-dioxolan-2-yl) propan-1-ol with hydrochloric acid to obtain 5-chloro-2-pentanone.

2. The process of claim 1, wherein said solution has a normality of 0.005 to 0.1.

3. The process of claim 1, wherein said solution has a normality of about 0.05.

4. The process of claim 1, wherein said alcoholic alkali metal hydroxide solution or alcoholic alkaline earth metal hydroxide solution is prepared using ethanol or methanol.

5. The process of claim 1, wherein said alkali metal hydroxide or alkaline earth metal hydroxide is selected from the group consisting of LiOH, NaOH, KOH, Mg(OH)$_2$, Ca(OH)$_2$, Sr(OH)$_2$, and Ba(OH)$_2$.

6. The process of claim 5, wherein said alkali metal hydroxide or alkaline earth metal hydroxide is NaOH, KOH or Ba(OH)$_2$.

* * * * *